(12) United States Patent
McNamara et al.

(10) Patent No.: US 6,423,298 B2
(45) Date of Patent: *Jul. 23, 2002

(54) PHARMACEUTICAL FORMULATIONS FOR AEROSOLS WITH TWO OR MORE ACTIVE SUBSTANCES

(75) Inventors: Daniel P. McNamara, Waterbury; George A. DeStefano, Brookfield, both of CT (US)

(73) Assignee: Boehringer Ingelheim Pharmaceuticals, Inc., Ridgefield, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/328,073

(22) Filed: Jun. 8, 1999

(51) Int. Cl.[7] .................................. A61K 9/12
(52) U.S. Cl. ........................... 424/45; 424/46
(58) Field of Search ...................... 424/45, 46

(56) References Cited

U.S. PATENT DOCUMENTS

| 5,225,183 A | * | 7/1993 | Purewal |
| 5,496,537 A | | 3/1996 | Henry |
| 5,589,156 A | | 12/1996 | Henry |
| 5,603,918 A | | 2/1997 | McNamara |
| 5,658,549 A | * | 8/1997 | Akehurst |
| 5,736,124 A | | 4/1998 | Akehurst et al. |
| 5,776,432 A | * | 7/1998 | Schultz |
| 5,817,293 A | | 10/1998 | Akehurst et al. |

FOREIGN PATENT DOCUMENTS

| CA | 2075058 | * | 8/1991 |
| EP | 0 499 344 A2 | | 11/1989 |
| EP | 0 372 777 | | 6/1990 |
| WO | 93/11773 | * | 6/1993 |
| WO | WO 94/13264 | | 6/1994 |
| WO | WO 96/18384 A1 | | 6/1996 |
| WO | 97/013219 | * | 1/1997 |
| WO | 97/47286 | * | 12/1997 |
| WO | WO 98/01147 | | 1/1998 |
| WO | WO 99/29296 | | 6/1999 |

OTHER PUBLICATIONS

Gennaro et al. (1985). Remington's Pharmaceutical Sciences, Mack Pub, PA, pp. 1662–1665.*

* cited by examiner

*Primary Examiner*—Jose' G. Dees
*Assistant Examiner*—M. Haghighatian
(74) *Attorney, Agent, or Firm*—Robert P. Raymond; Philip I. Datlow; Alan R. Stempel

(57) ABSTRACT

The present invention relates to new pharmaceutical formulations for aerosols with at least two or more active substances for administration by inhalation or by nasal route. Specifically, the invention relates to pharmaceutical preparations for propellant-driven metered dose aerosols using a fluorohydrocarbon (HFC) as propellant, which contain a combination of active substance of two or more active substances, wherein at least one active substance is present in dissolved form together with at least one other active substance in the form of suspended particles.

21 Claims, No Drawings

PHARMACEUTICAL FORMULATIONS FOR AEROSOLS WITH TWO OR MORE ACTIVE SUBSTANCES

The present invention relates to new pharmaceutical formulations for aerosols with at least two or more active substances for use by inhalation or by the nasal route.

STATE OF THE ART

In propellant-driven metered dose inhalers (MDI) the active substances can be formulated as solutions or suspensions. The vast majority of aerosol formulations for MDI's are prepared as suspensions, especially if the preparation contains more than one active substance. Formulations in the form of solutions are used only to a limited extent. In these cases, the formulations normally contain only one active substance.

As a rule, in a suspension, the chemical stability of the active substances is noticeably higher than in a solution. Additionally, in a suspension the active substance can be more highly concentrated than in a solution, with the result that suspension type formulation enable higher doses to be administered.

A major disadvantage of suspension-formulations is the fact that over time (e.g. during storage) the suspended particles clump together to form bigger, more or less stable agglomerates or form loose flakes, sediments or floating layers, or in the worst case, particle growth, which significantly impairs the pharmaceutical quality of the product. The size of the particles formed or the speed of particle growth are influenced by the solubility features of the liquid phase. Thus, ingress of humidity during storage or a desired increase in polarity, e.g. achieved by adding co-solvents, can have a devastating effect on the quality of the medical end product, particularly if the suspended particles have polar structure elements. The suspension can be physically stabilised by the addition of surfactants, by reducing the harmful effects of moisture and/or particle growth so that suspended particles can be held in suspension for longer.

Natural solution-type formulations are not affected by the problems of increasing particle size or de-mixing processes such as sedimentation or flocculation. However, in this case there is a serious risk of chemical degradation. A further disadvantage is the fact that the limited solubility of the ingredients can prevent administration in high doses. In the past, the chlorofluorohydrocarbons TG 11 (trichlorofluoromethane), TG 12 (dichlorodifluoromethane) and TG 114 (dichlorotetrafluoroethane) have proved particularly suitable as solvents. The solubility of the ingredients can be increased by the addition of co-solvents. In addition, it is usually necessary to take additional measures to chemically stabilise the dissolved components.

Up till now, CFCs such as the above-mentioned TG 11, for example, have often been used as propellants. However, since CFCs have been linked with the destruction of the ozone layer, their manufacture and use are being phased out. The intention is to replace them with special fluorohydrocarbons (HFC) which are less destructive to the ozone layer but have completely different solubility features. The toxicological profile and physico-chemical properties such as the steam pressure, for example, determine which HFCs are suitable for MDIs. The most promising representatives at present are TG 134a (1,1,2,2-tetrafluoroethane)and TG 227 (1,1,1,2,3,3,3-heptafluoropropane).

For inhalative treatment it may be desirable to have aerosol formulations with two or more active substances. In such cases the active substances are formulated in the necessary concentrations as solutions or suspensions, frequently giving rise to problems regarding the chemical stability of the individual substances or the degree of concentration which can be attained. Major problems are encountered if one of the active substances cannot be suspended or is unstable in a suspension-type formulation of this kind or if one of the active substances is chemically unstable or will not dissolve in a solution-type formulation of this kind, particularly when HFC is used as the propellant.

It is therefore one object of the present invention to develop a formulation for metering aerosols having two or more active substances which overcomes the above-mentioned disadvantages.

DESCRIPTION OF THE INVENTION

Surprisingly, it has been found that a plurality of active substances can be formulated as a solution and a suspension combined in one formulation.

The invention relates to stable aerosol formulations with fluorohydrocarbons as propellants, particularly TG 134a and/or TG 227, consisting of two or more active substances, wherein at least one active substance is formulated as a solution and at least one active substance is formulated as a suspension. The pharmaceutical preparation according to the invention is used for inhalative treatment, particularly for treating diseases of the pharynx and respiratory tract, e.g. asthmatic diseases and COPD.

DETAILED DESCRIPTION OF THE INVENTION

In one embodiment a medicinally useful combination of two or more active substances is used, containing beclometasone, budesonide, cromoglycinic acid, fenoterol, flunisolide, fluticasone, ipratropium bromide, nedocromil, orciprenaline, oxitropium bromide, reproterol, salbutamol (albuterol), salmeterol, terbutalin, N-[[2,2-dimethyl-4(2-oxo-2H-pyridin-1-yl)-6-trifluoromethyl-2H-1-benzopyran-3-yl]methyl]-N-hydroxy-acetamide, the esters, salts and/or solvates thereof. Which of the above-mentioned active substances is formulated as a solution and which as a suspension in the preparation according to the invention depends on the particular combinations of active substance and can be determined relatively quickly by solution and suspension trials.

In a preferred embodiment, one or more of the following active substances are suspended: budesonide, cromoglycinic acid, nedocromil, reproterol and/or salbutamol (albuterol) or the esters, salts and/or solvates derived from these compounds and one or more of the following substances are dissolved: beclomethasone, fenoterol, ipratropium bromide, orciprenaline and/or oxitropium bromide, N-[[2,2-dimethyl-4-(2-oxo-2H-pyridin-1-yl)-6-trifluoromethyl-2H-1-benzopyran-3-yl]methyl]-N-hydroxy-acetamide or the esters, salts and/or solvates derived from these compounds. Embodiments having two different active substances are preferred.

A particularly preferred embodiment contains dissolved ipratropium bromide, particularly combined with salbutamol sulphate (albuterol sulphate) as the suspended active substance.

In all the embodiments, the active substances are used in a therapeutically effective quantity, i.e. in a quantity that can induce a successful treatment. The concentration of the active substances and the volume per stroke of spray are adjusted in such a way that the quantity of active substance which is medically necessary or recommended is released by a single spray or by a few sprays.

One embodiment relates to formulations in which the suspended particles are stabilised by the addition of surfactant substances (surfactants) or other suspension-stabilising agents to stabilise the suspended particles against physical changes. The benefit of this is that the particle size will remain pharmaceutically acceptable even over lengthy periods, e.g. during storage. Preferred particle sizes are up to 20 μm, whilst particularly preferred particle sizes are between 5 and 15 μm, best of all not exceeding 10 μm. The advantage of these particle sizes is that the particles are small enough to penetrate deeply into the lungs but not so small as to be breathed out again with the exchanged air.

Suitable surfactants and suspension-stabilising agents include all pharmacologically acceptable substances which have a lipophilic hydrocarbon group and one or more functional hydrophilic groups, especially $C_{5-20}$ fatty alcohols, $C_{5-20}$ fatty acids, $C_{5-20}$ fatty acid esters, lecithin, glycerides, propyleneglycol esters, polyoxyethylenes, polysorbates, sorbitan esters and/or carbohydrates. $C_{5-20}$ fatty acids, propyleneglycol diesters and/or triglycerides and/or sorbitans of the $C_{5-20}$ fatty acids are preferred, whilst oleic acid and sorbitan mono-, di- or trioleates are particularly preferred. Alternatively, toxicologically and pharmaceutically acceptable polymers and block-polymers can be used as suspension-stabilising agents. The surfactants used are either non-fluorinated or partially fluorinated or perfluorinated, the term fluorinated referring to the exchange of hydrogen radicals bound to the carbon for fluorine radicals. The quantity of surfactant may be up to 1:1 based on the proportion by weight of the suspended active substances; amounts of 0.0001:1 to 0.5:1 are preferred, whilst amounts of from 0.0001:1 to 0.25:1 are particularly preferred.

A further advantage of the above surfactants is that they can also be used as valve lubricants. Therefore, one embodiment relates to formulations in which said surfactants are added as valve lubricants.

In another embodiment the solubility of at least one active substance to be dissolved is increased by the addition of one or more co-solvents. This has the advantage that the active substance or substances to be dissolved can be formulated in higher concentrations. The addition of co-solvent must not exceed the critical threshold of polarity of the liquid phase at which one of the disadvantages described above begins to affect the suspended particles of active substance.

Suitable co-solvents are pharmacologically acceptable alcohols such as ethanol, esters or water or mixtures thereof; ethanol is preferred. The concentration of the co-solvent in relation to the total formulation may be from 0.0001 to 50 wt.-%, preferably 0.0001 to 25 wt.-%. In another embodiment a concentration of 0.0001 to 10 wt.-% is preferred whilst particularly preferred embodiments are those wherein just enough alcohol is added to dissolve the active substance which has to be dissolved.

In another embodiment, other common propellants are added to the HFC propellant. These added propellants may be, beside other HFCs, saturated lower hydrocarbons such as propane, butane, isobutane or pentane provided that the mixture is pharmacologically acceptable.

In one embodiment, stabilisers are added to the formulation, with a beneficial effect on the pharmaceutical stability of the active substances even over lengthy periods, e.g. during storage. In the context of the invention, stabilisers denotes those substances which prolong the durability and usability of the pharmaceutical preparation by preventing or delaying chemical changes in the individual ingredients, particularly the active substances, e.g. caused by subsequent reactions or degradation, or those which prevent biological contamination. Stabilisers which are preferred for this purpose are those which influence the pH of the liquid phase, such as acids and/or the salts thereof, particularly suitable substances are hydrochloric acid, sulphuric acid, nitric acid, phosphoric acid, ascorbic acid, citric acid and the salts thereof. In addition, preferred bactericides, fungicides etc. are benzalkonium chloride or ethylene diamine tetraacetate. Citric acid is most preferred. The concentration of the stabilisers may be up to 1000 ppm, preferably up to 100 ppm and most preferably 20 to 40 ppm.

One particularly preferred embodiment comprises suspended salbutamol sulphate (albuterol sulphate), dissolved ipratropium bromide, ethanol as co-solvent and citric acid as stabiliser.

EXAMPLES

Example 1

In a solution of liquefied 89.96 g (1 mol, 89.71 wt.-%) of TG 134a and 10.03 g (218 mmol, 10.00% by weight) of ethanol are dissolved 37 mg (0.09 mmol, 0.037 wt.-%) of ipratropium bromide and 4 mg (20 μmol, 0.004% by weight) of citric acid and 210.5 mg (0.88 mmol, 0.21% by weight) of salbutamol sulphate (albuterol sulphate) are suspended together with 0.05% by weight of surfactant (e.g. 50 mg (177 mmol) of oleic acid).

Example 2

Analogous to Example 1 using TG 227 as the propellant gas instead of TG 134a.

Example 3

Disodium chromoglycate is suspended in liquefied P134 and a small amount of ethanol and fenoterol hydrobromide is dissolved therein.

Example 4 analogous to example 3 using TG 227 as propellant gas instead of TG 134a.

What is claimed is:

1. A pharmaceutical preparation for propellant driven metered dose inhalers having a fluorohydrocarbon as propellant, which comprises a combination of two or more active substances in a liquid phase wherein at least one active substance is present in dissolved form in the liquid phase by the use of one or more co-solvents other than the fluorohydrocarbon and at least one other active substance is in the form of suspended particles in the liquid phase.

2. Pharmaceutical preparation according to claim 1, wherein there are two active substances.

3. The pharmaceutical preparation according to claim 1, wherein the propellant is TG 134a, TG 227 or combinations thereof.

4. The pharmaceutical preparation according to claim 3, wherein said one or more co-solvents comprises one or more pharmacologically tolerable alcohols, a pharmacologically tolerable ester, water or a mixture thereof.

5. The pharmaceutcal preparation according to claim 3, wherein said one or more co-solvents is ethanol.

6. The pharmaceutical preparation according to claim 5 wherein the ethanol is present in a concentration of up to 25% by weight, based on the quantity of liquefied propellant.

7. The pharmaceutical preparation according to claim 6, wherein the ethanol is present in a concentration of up to 10% by weight, based on the quantity of liquefied propellant.

8. The pharmaceutical preparation according to claim 7, wherein the composition is stabilised by one or more stabilisers.

9. The pharmaceutical preparation according to claim 8, wherein said one or more stabilisers is selected from one or more acids, salts and combinations thereof.

10. The pharmaceutical preparation according to claim 9 wherein the stabiliser(s) is hydrochloric acid, sulphuric acid, nitric acid, phosphoric acid, ascorbic acid, citric acid, benzalkonium chloride, ethylene diamine tetraacetic, their salts or combinations thereof.

11. The pharmaceutical preparation according to claim 10, wherein the stabiliser is citric acid.

12. The pharmaceutical preparation according to claim 11, wherein the stabiliser is present in an amount of up to 100 ppm.

13. The pharmaceutical preparation according to claim 12, wherein the stabiliser is present in an amount of up to 40 ppm.

14. The pharmaceutical preparation according to claim 10, wherein the preparation contains one or more surfactants or suspension-stabilising agents.

15. The pharmaceutical preparation according to claim 14, wherein the one or more surfactants is selected from $C_{5-20}$ fatty alcohols, $C_{5-20}$ fatty acids, $C_{5-20}$ fatty acid esters, lecithin, glycerides, propyleneglycol esters, polyoxyethanes, polysorbates, sorbitan esters, carbohydrates and combinations thereof.

16. The pharmaceutical preparation according to claim 14 wherein the one or more surfactants is selected from $C_{5-20}$ fatty acids, their esters and combinations thereof.

17. The pharmaceutical preparation according to claim 14 wherein the one or more surfactants is selected from oleic acid, sorbitan mono-, di- or trioleate and combinations thereof.

18. The pharmaceutical preparation according to claim 14, wherein the one or more surfactants is oleic acid.

19. The pharmaceutical preparation according to claim 14 wherein the one or more surfactants or suspension-stabilising agents is selected from a toxicologically acceptable polymer, block-polymer and combinations thereof.

20. The pharmaceutical preparation according to claim 1, wherein the active substance combination contains beclomethasone, budesonide, cromoglycinic acid, fenoterol, flunisolide, fluticasone, ipratropium, nedocromil, orciprenaline, oxitropium bromide, reproterol, salbutamol, salmeterol (albuterol), terbutalin, N-[[2,2-dimethyl-4-(2-oxo-2H-pyridin-1-yl)-6-trifluoromethyl-2H-1-benzopyran-3-yl]methyl]-N-hydroxy-acetamide, the esters, salts, solvates or combinations thereof.

21. The pharmaceutical preparation according to claim 20, wherein the active substance combination contains salbutamol sulphate (albuterol sulphate) and ipratropium bromide.

* * * * *

UNITED STATES PATENT AND TRADEMARK OFFICE
CERTIFICATE OF CORRECTION

PATENT NO.    : 6,423,298 B2
DATED         : July 23, 2002
INVENTOR(S)   : McNamara, D. P. et al.

It is certified that error appears in the above-identified patent and that said Letters Patent is hereby corrected as shown below:

<u>Title page,</u>
Insert the following Item:
-- [30], Foreign Application Priority Data,
      Jun. 18, 1998 (DE)..........198 27 178.
      Sep. 19, 1998 (DE)..........198 42 963 --.

Signed and Sealed this

Third Day of June, 2003

JAMES E. ROGAN
*Director of the United States Patent and Trademark Office*